United States Patent [19]

Ohta et al.

[11] 4,453,397
[45] Jun. 12, 1984

[54] GAS DETECTING SENSOR

[75] Inventors: Minoru Ohta; Yutaka Hattori, both of Okazaki; Tomio Kawakami, Nishio; Michitoshi Onoda, Toyohashi, all of Japan

[73] Assignee: Nippon Soken, Inc., Nishio, Japan

[21] Appl. No.: 354,794

[22] Filed: Mar. 4, 1982

[30] Foreign Application Priority Data

Aug. 17, 1981 [JP] Japan .................................. 56-128629
Aug. 18, 1981 [JP] Japan .................................. 56-129176
Nov. 30, 1981 [JP] Japan .................................. 56-192477

[51] Int. Cl.$^3$ ............................................. G01N 27/12
[52] U.S. Cl. ............................................. 73/23; 338/34
[58] Field of Search .................. 73/23, 27 R; 338/34; 422/98; 324/71.5

[56] References Cited

U.S. PATENT DOCUMENTS

| | | | |
|---|---|---|---|
| 3,933,028 | 1/1976 | Laud et al. ................................ | 73/23 |
| 4,007,435 | 2/1977 | Tien ......................................... | 73/23 |
| 4,012,709 | 3/1977 | Logothetis et al. ..................... | 73/23 |
| 4,151,503 | 4/1979 | Cermak et al. ......................... | 73/27 R |
| 4,377,944 | 3/1983 | Hishii et al. ............................ | 73/23 |

FOREIGN PATENT DOCUMENTS 2908916 9/1980 Fed. Rep. of Germany .......... 73/23

*Primary Examiner*—Stephen A. Kreitman
*Attorney, Agent, or Firm*—Cushman, Darby & Cushman

[57] ABSTRACT

A gas detecting sensor for precisely detecting the partial pressure of oxygen gas in the exhaust gases without being affected by the change of the temperature of the environment thereof, is disclosed. The sensor is provided with a ceramic base member, a film-shaped gas sensing element having a characteristic in response to the partial pressure of oxygen gas which is held by the base member so as to be exposed to the exhaust gases, a film shaped temperature sensing element having temperature coefficient of resistance substantially equal to that of the gas sensing element, which is held by the base member so as to be isolated from the exhaust gases, and an electric current wherein the gas and the temperature sensing elements are connected to each other in series to form an electric junction therebetween, from which output voltage is taken. In the preferred embodiment, the temperature sensing element is embedded within the base member and a heating member is further provided for maintaining both elements within a temperature range in which temperature coefficient of resistance of both elements are substantially equal to each other.

8 Claims, 19 Drawing Figures

FIG.16
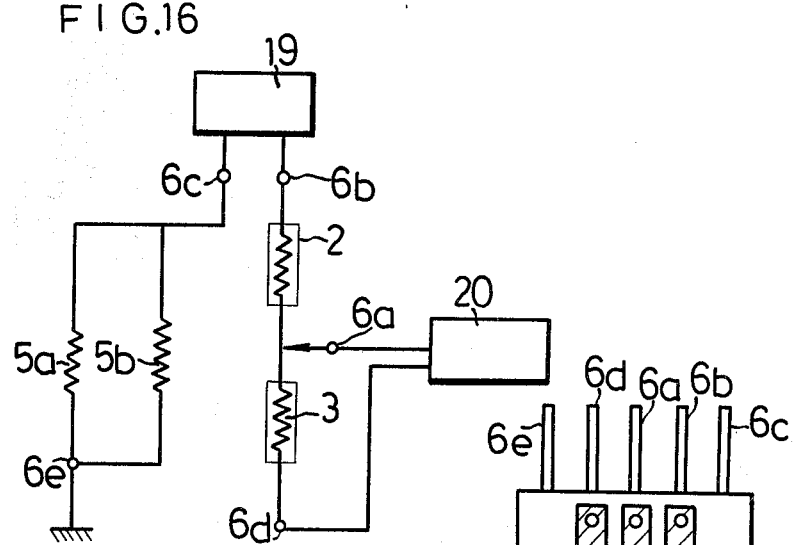
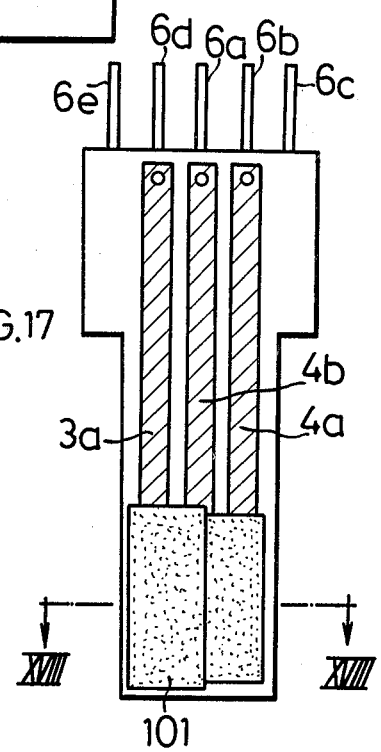
FIG.17
FIG.18
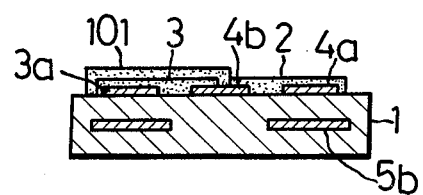

4,453,397

GAS DETECTING SENSOR

BACKGROUND OF THE INVENTION

The present invention relates to a gas detecting sensor, particularly to a sensor for detecting the partial pressure of oxygen gas contained within exhaust gases discharged from an internal combustion engine of an automobile or the like and measuring air to fuel ratio of the combustion mixture to be supplied into the internal combustion engine.

Recently, "lean burn system" that is, the system of operating an internal combustion engine with an air to fuel ratio larger than the stoichiometric ratio so as to reduce harmful components contained within the exhaust gases and lower the fuel consumption has been proposed and employed practically.

The above described "lean burn system" requires a detecting means for accurately detecting air to fuel ratio in a range of lean mixtures. U.S. Pat. Nos. 3,933,028 and 4,012,709 disclose examples of such a detecting sensor as described above.

These detecting sensors are provided with a sensing element formed of cobalt monoxide (CoO) or an alloy of cobalt monoxide(CoO) and magnesium monoxide(MgO).

These detecting sensors are further provided with a heating means so as to surround the sensing element for maintaining the sensing element at a predetermined temperature, for example 900° C. in order to prevent cobalt monoxide from changing into tricobalt tetroxide ($Co_3O_4$) and to compensate the temperature change.

However, the above described conventional detecting sensor has such a problem that it is difficult to maintain the temperature of the sensing element at a predetermined temperature without being affected by the change in the temperature and the flowing volume of the exhaust gases.

Generally, the electric resistance of the sensing element changes due to the change in the temperature of its environment and the change in the chemical constituent of the exhaust gases. Therefore, when the temperature of the exhaust gases is changed, the partial pressure of oxygen gas cannot be precisely measured so that the air to fuel ratio of the combustion mixture cannot be precisely controlled.

Furthermore, in order to maintain the temperature of the sensing element at a predetermined temperature without being affected by the change in the temperature and the flowing volume of the exhaust gases, the control circuit having the complex structure is required.

Accordingly, one object of the present invention is to provide a gas detecting sensor for precisely measuring the partial pressure of oxygen gas contained within the exhaust gases when the temperature of the exhaust gases is largely changed or when the sensor is positioned in the oxidizing atmosphere or the reducing atmosphere.

Another object of the present invention is to provide a small sized gas detecting sensor having a simple structure, by which the partial pressure of oxygen gas can be precisely measured.

DESCRIPTION OF THE DRAWINGS

Other objects and advantages of the invention will become apparent from the following description of embodiments thereof with reference to the accompanying drawings wherein:

FIG. 16 is an electric circuit diagram of the sixth embodiment;

FIG. 17 is a plan view of a seventh embodiment;

FIG. 18 is a sectional view taken along the line XVIII—XVIII of FIG. 17; and

SUMMARY OF THE INVENTION

Figure 1:
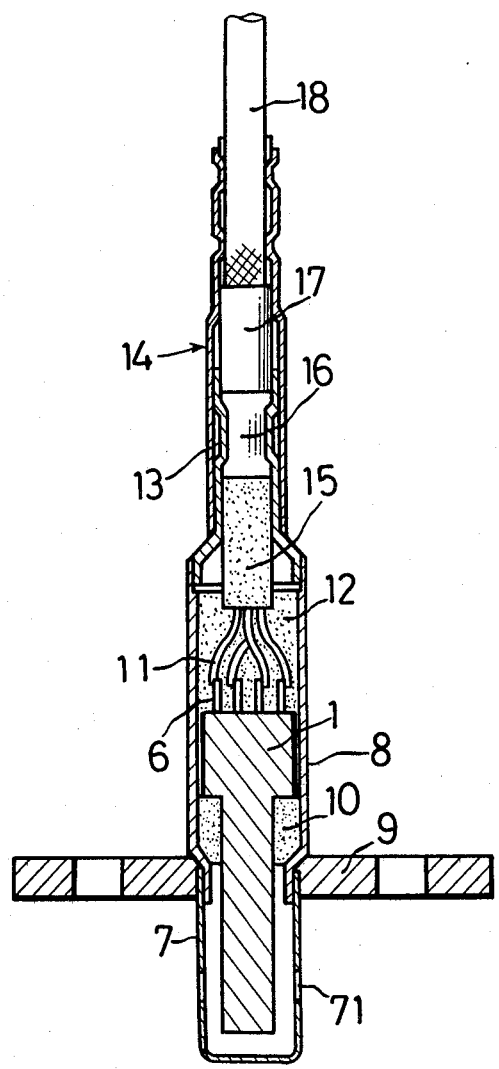
FIG. 1 is a sectional view of a gas detecting device wherein a gas detecting sensor of a first embodiment of the present invention is accommodated.
Figure 2:
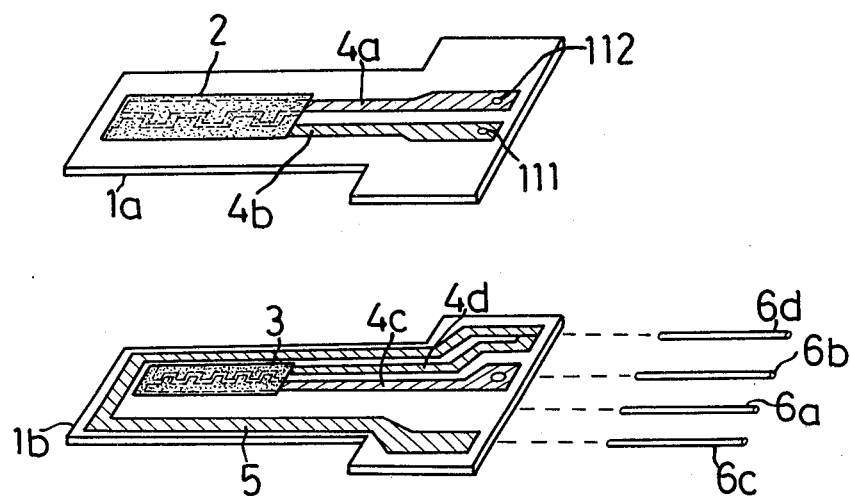
FIG. 2 is an exploded perspective view illustrating the assembling state of parts of a detecting sensor of a first embodiment of the present invention.
Figure 3:
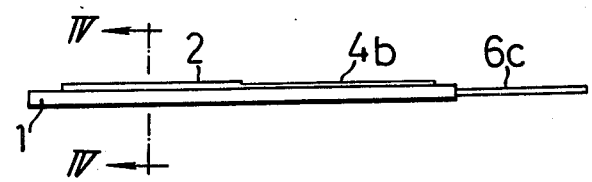
FIG. 3 is a side view of the detecting sensor of the first embodiment.
Figure 4:
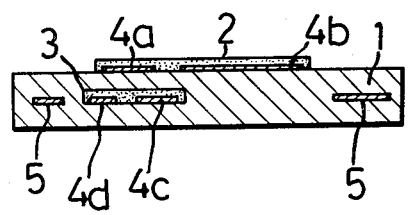
FIG. 4 is a sectional view taken along the line IV—IV of FIG. 3.

The gas detecting sensor of the present invention is provided with a heat resistant and electrically insulating base member, a film shaped first sensing element, and a film shaped second sensing element having substantially the same temperature coefficient of resistance of the first sensing element. The second sensing element is embedded within the base member or formed on the surface of the base member in such a state as being covered with a layer formed of such a material as to be impervious to exhaust gases. And output voltage is taken from the electric junction of both elements.

DETAILED DESCRIPTION OF THE INVENTION

Hereinafter, the present invention will be explained in accordance with the embodiments with reference to the accompanying drawings.

FIGS. 1 to 4 illustrate a first embodiment of a gas detecting sensor according to the present invention.

The gas detecting sensor of a first embodiment is provided with a base body 1 made of alumina for retaining a gas sensing element 2, a temperature sensing element 3, electrodes 4a, 4b, 4c, 4d and a heater 5, and lead wires 6a, 6b, 6c, 6d.

The structure of the gas detecting sensor of the first embodiment will be explained in detail as well as the producing method thereof.

At first, a pair of thin plates 1a, 1b made of alumina green sheet, respectively, are prepared. Then, a pair of film-shaped electrodes 4a, 4b made of platinum, platinum-rhodium or the like, respectively, are formed on the thin plate 1a by printing method. The thin plate 1a is provided with through holes 111, 112 so as to be opposed to each one end of the electrodes 4a, 4b, respectively. Within the through holes 111, 112, electrodes are also formed so as to be electrically connected to the electrodes 4a, 4b, respectively.

The other end portion of each of the electrodes 4a, 4b is formed like teeth of a comb and the teeth-shaped end portions of the electrodes 4a, 4b are opposed to each other.

On the thin plate 1b, a film-shaped heater 5 made of platinum, platinum-rhodium alloy, tungsten, molybdenum-manganese alloy or the like is formed by printing method. Furthermore, an electrode 4c is formed on the thin plate 1b so as to extend under the electrode 4a and an electrode 4d is formed on the thin plate 1b so as to be opposed to the electrode 4c in the teeth-shaped end portions thereof.

A film shaped temperature sensing element 3 made of zirconium oxide ($ZrO_2$) in which niobium oxide ($Nb_2O_5$) dissolves in sold phase is formed on the electrodes 4c, 4d so as to cover the teeth-shaped end portions thereof by printing method.

The other end of the electrode 4d is electrically connected to one end of the heater 5.

Next, the thin plate 1a is laid on the thin plate 1b so that the under surface of the thin plate 1a contacts with the upper surface of the thin plate 1b.

At the time, one end of each of lead wires 6a, 6b, 6c, 6d made of platinum, platinum-rhodium alloy or the like is disposed between the thin plates 1a, 1b so that the lead wire 6a is electrically connected to the electrode 4b of the thin plate 1a through the electrode formed within the through hole 111 thereof, the lead wire 6b is electrically connected to the electrode 4a of the thin plate 1a through the electrode 4c of the thin plate 1b and the electrode formed within the through hole 112 and the lead wires 6d, 6c are electrically connected to both ends of the heater 5 of the thin plate 1b, respectively.

The combined thin plates 1a, 1b are fired at 1500° C. to 1600° C. for about 5 hours within an electric furnace. The thin plates 1a, 1b are sintered to form an integral base body 1.

Consequently, within the base body 1, the film shaped heater 5, the film shaped temperature sensing element 3 and the electrodes 4c, 4d are formed while on the surface of the base body 1, the film shaped electrodes 4a, 4b are formed.

The lead wires 6a, 6b, 6c, 6d are firmly fixed to the thin plates 1a, 1b due to the shrinkage occurring in the sintering process.

Then, the paste of cobalt monoxide is printed on the electrodes 4a, 4b so as to cover the teeth shaped end portions thereof. After being dried, the printed base body 1 is fired at about 900° C. for about two hours within an electric furnace to form a gas sensing element 2 on the base body 1.

As shown in FIG. 1, the gas detecting sensor produced by the above described method is accomodated within a protecting cover 7 made of heat resistant metal and provided with a hole 71 through which exhaust gases are introduced therewithin, and a pipe member 8 which is connected to the protecting cover 7.

In the connecting portion of the protecting cover 7 and the pipe member 8, a flange member 9 is fixed for mounting the gas detecting sensor to an exhaust pipe.

The base body 1 is supported by a retaining member 10 made of a sintered body of alumina or the like within the pipe member 8.

And the upper portion of the base body 1, the lead wires 6 and sub-lead wires 11 made of heat resistant metal such as stainless steel, which are connected to the lead wires 6 are fixed within the pipe member 8 by means of inorganic adhesive 12.

To the pipe member 8, pipe members 13, 14 are connected in order. The sub-lead wires 11 are inserted within an insulating pipe 15 made of alumina or the like, a bush 16 made of fluorine-contained rubber or the like and a heat resistant rubber member 17 made of silicon rubber or the like.

The sub-lead wires 11 extending outside of the pipe member 14 are covered with a covering member 18.

Figure 5:
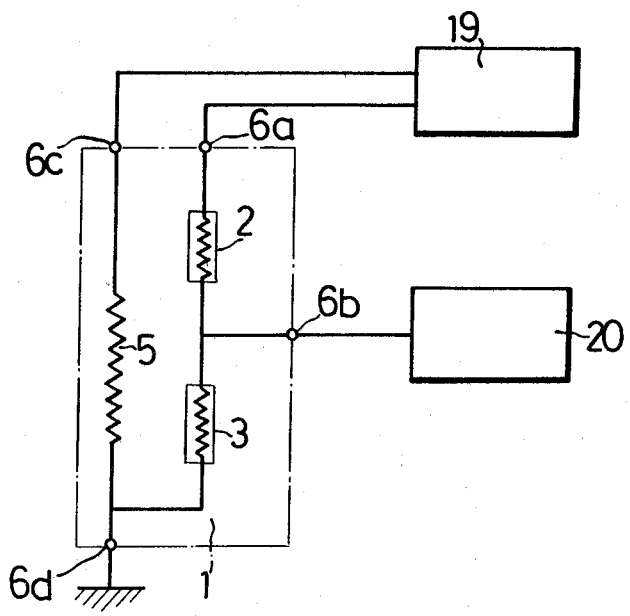
FIG. 5 is an electric current diagram of the first embodiment.

FIG. 5 illustrates a detecting circuit of the gas detecting sensor having the above described structure.

The gas sensing element 2 is electrically connected to the temperature sensing element 3 in series while the elements 2, 3 and the heater 5 are connected to an electric power source 19 in parallel.

The lead wire 6b which is connected to the lead wire between the elements 2, 3 is connected to a control circuit 20 comprising a comparator and a computer which controls the air to fuel ratio of the combustion mixture of the engine by the output voltage of the comparator.

In the gas detecting sensor of the first embodiment, the electric resistance of the gas sensing element 2 changes in response to the change of the chemical constituent of the exhaust gases, that is the air to fuel ratio of the combustion mixture.

Figure 6:
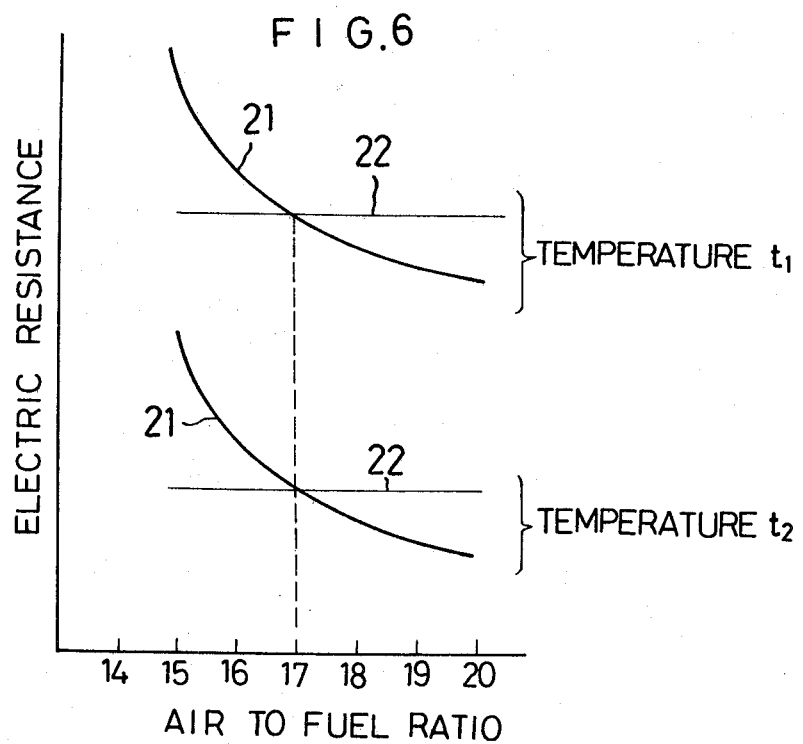
FIG. 6 is a graph showing the relation of the electric resistance of the gas sensing element and the temperature sensing element of the present invention to the air to fuel ratio.

For example, as the air to fuel ratio is increased, namely the fuel content of the combustion mixture is decreased, the electric resistance of the gas sensing element 2 is decreased as shown by the line 21 in FIG. 6.

In contrast, since the temperature sensing element 3 is embedded within the base body 1 so as not to contact with the exhaust gases substantially, the electric resistance thereof always shows a specific value which only depends on the temperature of the environment thereof as shown by the line 22 in FIG. 6, without being affected by the air to fuel ratio of the combustion mixture.

When the temperature of the environment of the detecting sensor rises from $t_1$ to $t_2$, the electric resistance of each of the gas sensing element 2 and the temperature sensing element 3 is decreased.

Since the temperature coefficient of resistance of the element 2 is nearly equal to that of the element 3, the air to fuel ratio at which the electric resistance of the element 2 is equal to that of the element 3 is not changed when the temperature rises from $t_1$ to $t_2$.

And the ratio of the electric resistance of the gas sensing element 2 to that of the temperature sensing element 3 is constant at a predetermined air to fuel ratio when the temperature of the environment is changed.

Therefore, the output voltage obtained from the detecting circuit shown in FIG. 5 of the gas detecting sensor of a first embodiment only depends on the change of the air to fuel ratio without being affected by the temperature of the environment.

Figure 7:
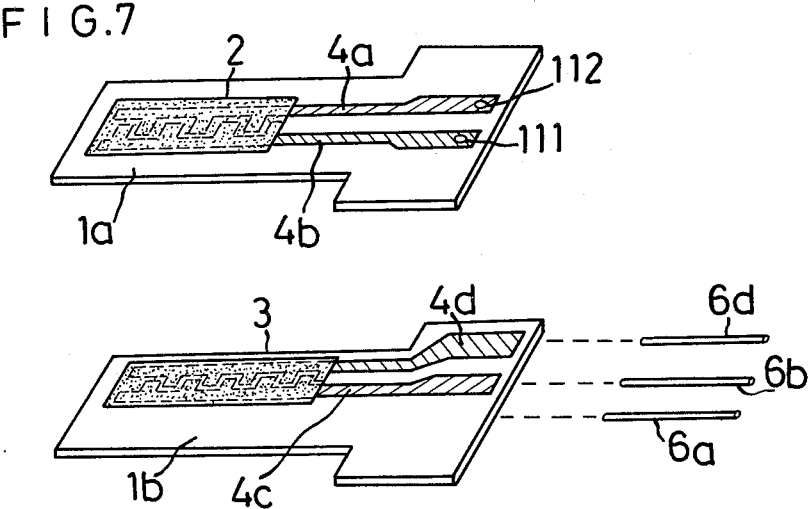
FIG. 7 is an exploded perspective view illustrating the assembling state of parts of a detecting sensor of a second embodiment of the present invention.

FIG. 7 illustrates a second embodiment of the sensor according to the present invention.

In the gas detecting sensor of the second embodiment, both of the gas sensing element 2 and the temperature sensing element 3 are formed of titanium oxide ($TiO_2$). And any heating means is not provided.

On the alumina thin plate 1a, the electrodes 4a, 4b and the gas sensing element 2 are formed and on the alumina thin plate 1b, the electrodes 4c, 4d and the temperature sensing element 3 are formed. These thin plates 1a, 1b are sintered after the lead wires 6a, 6b, 6d are disposed therebetween to form an integral base body.

The gas sensing element 2 carries catalyst such as platinum, platinum-rhodium alloy or the like.

According to the second embodiment, the elements 2, 3 are made of the same material, both elements exhibit the same temperature coefficient of resistance at any temperature. Consequently, the gas detecting sensor of the second embodiment does not require any heating means for measuring the precise air to fuel ratio.

Figure 8:
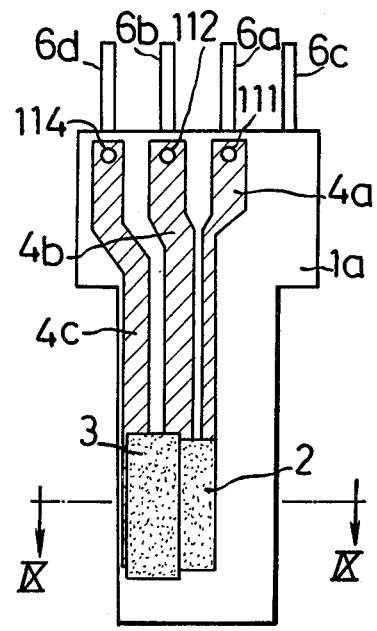
FIG. 8 is a plan view of the detecting sensor of a third embodiment of the present invention.
Figure 9:
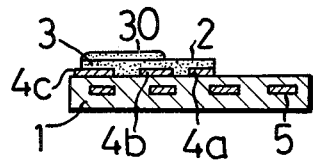
FIG. 9 is a sectional view taken along the line IX—IX of FIG. 8.
Figure 10:
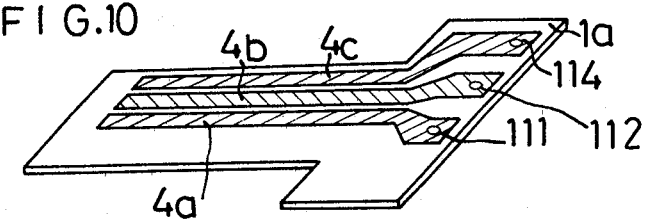
FIG. 10 is an exploded perspective view illustrating the assembling state of parts of a detecting sensor of a fourth embodiment of the present invention.

FIGS. 8 to 10 illustrate a third embodiment of the sensor according to the present invention.

As shown in FIG. 8, on one thin plate 1a, film-shaped electrodes 4a, 4b, 4c made of heat resistant metal such as platinum, platinum-rhodium alloy or the like are formed by screen printing method. These electrodes 4a, 4b, 4c are also formed on the surface defining through holes 111, 112, 114.

As shown in FIG. 10, on the other thin plate 1b, a film-shaped heater 5 made of metal such as platinum, platinum-rhodium alloy, tungsten, molybdenum-manganese alloy or the like are formed by screen printing method along the periphery thereof and in the portions opposed to one part of each of the electrodes 4a, 4b.

The thin plate 1a is laid on the thin plate 1b after one end of each of lead wires 6a, 6b, 6c, 6d is disposed therebetween.

The lead wires 6a, 6b, 6d are disposed so that one end of each lead wire is opposed to the through hole 111, 112 or 114 which is formed on the thin plate 1a while the end of the lead wire 6c contacts with one end of the heater 5 formed on the sheet 1b.

The combined plates 1a, 1b are pressed while being heated and fired at 1500° C. to 1600° C. for about 5 hours within an electric furnace. As a result, the plates 1a, 1b are sintered to form an integral base body provided with the film-shaped heater 5 therewithin and the film-shaped electrodes 4a, 4b, 4c thereon.

At the same time, the lead wires 6a, 6b, 6c, 6d are firmly fixed to the plates 1a, 1b due to the shrinkage occurring in the sintering process.

As a result, the lead wires 6a, 6b are connected to the electrodes 4a, 4b, respectively, and the lead wire 6c is connected to one end of the heater 5 while the lead wire 6d is connected to the electrode 4c and the other end of the heater 5.

Next, the paste of cobalt monoxide in which magnesium monoxide dissolves in solid phase is printed on the surface of the base body so as to cover one portion of each of the electrodes 4a, 4b, 4c, respectively, by screen printing method. After being dried, the printed base body is fired at 1150° C. for 2 hours within an electric furnace.

Then, the layer of cobalt monoxide which is formed so as to cover the electrodes 4b, 4c is coated with the paste of borosilicate glass for forming the temperature sensing element 3.

The obtained base body is dried and fired at about 1050° C. for 15 minutes.

As a result, the detecting sensor provided with the gas sensing element 2 formed on the electrodes 4a and 4b and the temperature sensing element 3 formed on the electrodes 4b, 4c and covered by the glass layer 30 as illustrated in FIG. 9 is obtained.

Since the temperature sensing element 3 is substantially covered with the coating layer 30 which is impermeable to gas, the electric resistance of the temperature sensing element 3 only depends on the temperature of the environment thereof without being affected by the partial pressure of oxygen gas contained within the exhaust gases.

And since the temperature sensing element 3 is formed of the same material as that of the gas sensing element 2, the precise air to fuel ratio can be measured by the gas detecting sensor of the third embodiment regardless of the temperature change.

Figure 11:
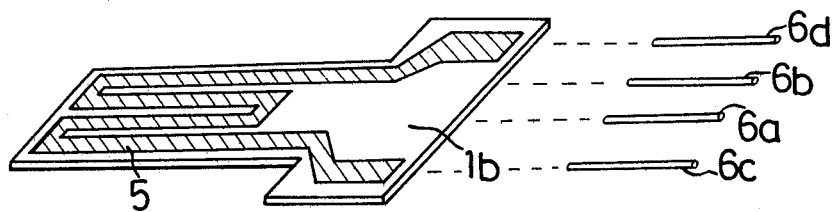
FIG. 11 is a sectional view of a gas detecting device wherein a gas detecting sensor of a fifth embodiment of the present invention is accommodated.
Figure 11:
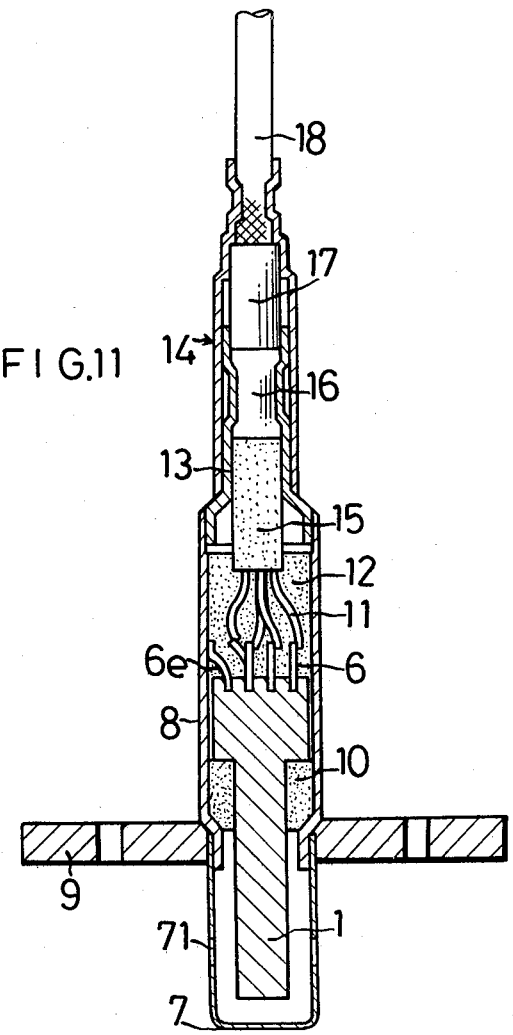
Figure 14:
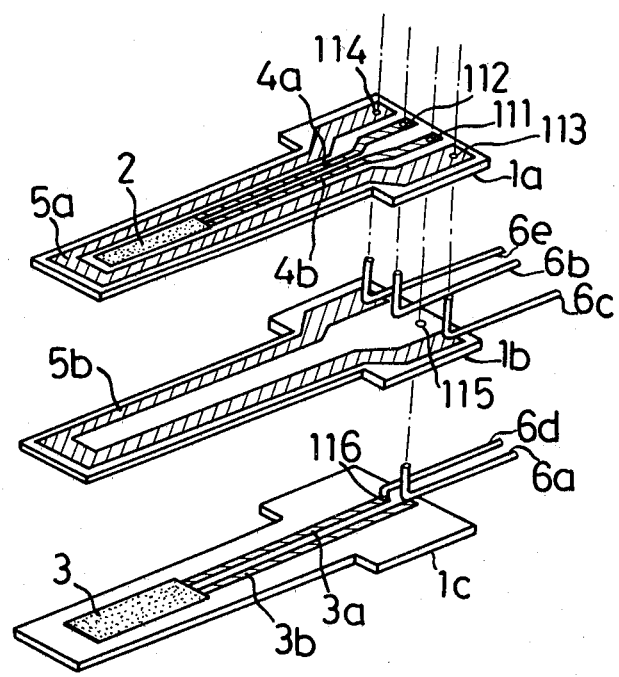
FIG. 14 is an exploded perspective view illustrating the assembling state of parts of a detecting sensor of a sixth embodiment of the present invention.

FIGS. 11 and 14 illustrate a fourth embodiment of the sensor according to the present invention.

As shown in FIG. 11, to the top end of the base body 1, five lead wires are fixed. One lead wire 6e is fixed to the pipe member 8.

Figure 12:
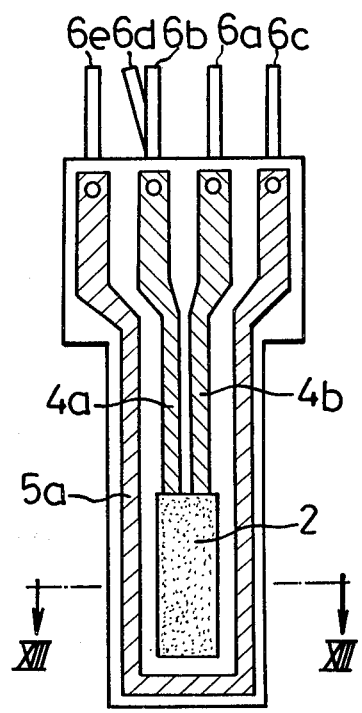
FIG. 12 is a plan view of the fifth embodiment.
Figure 13:
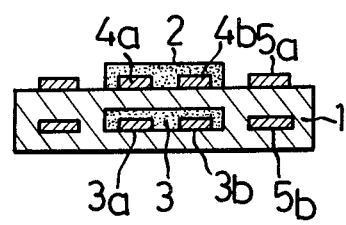
FIG. 13 is a sectional view taken along the line XIII—XIII of FIG. 12.

The gas detecting sensor of the fourth embodiment will be explained in detail with reference to FIGS. 12 to 14.

As shown in FIG. 14, on the thin plate 1a, a pair of film-shaped electrodes 4a, 4b made of heat resistant metal such as platinum, platinum-rhodium alloy or the like are printed so as to be spaced from each other by screen printing method. These electrodes 4a, 4b are also formed on the surfaces defining the through holes 111, 112 formed in the thin plate 1a.

Along the periphery of the thin plate 1a, a film-shaped heater 5a made of metal such as platinum, platinum-rhodium alloy, tungsten, molybdenum-manganese alloy or the like is printed by screen printing method.

The heater 5a is also formed on the surfaces defining the through holes 113, 114.

Along the periphery of the thin plate 1b, a heater 5b is printed so as to be opposed to the electrodes 4a, 4b formed on the thin plate 1a, by screen printing method.

On the thin plate 1c, a pair of film-shaped electrodes 3a, 3b made of heat resistant metal such as platinum, platinum-rhodium alloy or the like are printed by screen printing method so as to be spaced from each other.

And a film-shaped sensing element 3 made of cerium oxide ($CeO_2$) is printed so as to cover one portion of each of the electrodes 3a, 3b.

Then, the thin plates 1a, 1b, 1c are combined after the lead wires 6a, 6b, 6c, 6d, 6e are disposed therebetween.

The lead wires 6b, 6c, 6e are disposed between the thin plates 1a, 1b so that one end of each lead wire is opposed to the through hole 112, 113 or 114 formed in the plate 1a while the lead wires 6a, 6d are disposed between the thin plates 1b, 1c so that one end of each lead wire is opposed to the through hole 115 formed in the plate 1b or the through hole 116 formed in the plate 1c.

The combined plates 1a, 1b, 1c are pressed while being heated, and fired at 1500° C. to 1600° C. for about 5 hours within an electric furnace.

As a result, the plates 1a, 1b, 1c are sintered to form an integral base body provided with the film shaped electrodes 3a, 3b, the film-shaped temperature sensing element 3 and the film-shaped heater 5b, which are formed therewithin, and the film-shaped electrodes 4a, 4b, the film-shaped heater 5a which are formed thereon.

At the same time, the lead wires 6a, 6b, 6c, 6d, 6e are firmly fixed to the plates 1a, 1b, 1c due to the shrinkage occurring in the sintering process.

Next, the paste of cobalt monoxide in which magnesium monoxide and nickel monoxide dissolve in solid phase is printed so as to cover the electrodes 4a, 4b by screen printing method. After being dried, the printed base body is fired at about 1150° C. for 2 hours within an electric furnace. The preferable composition ratio of the gas sensing element is 20 to 60 mol % of cobalt monoxide, 20 to 60 mol % of magnesium oxide and 10 to 50 mol % of nickel monoxide.

As a result, the gas sensing element 2 is formed on one portion of the electrodes 4a, 4b while the temperature sensing element 3 is formed on one portion of the electrodes 3a, 3b within the base body 1.

The resistance-temperature characteristic of the obtained gas sensing element 2 and the obtained temperature sensing element 3 is measured by disposing the elements 2, 3 within an electric furnace and increasing the heating temperature thereof.

Figure 15:
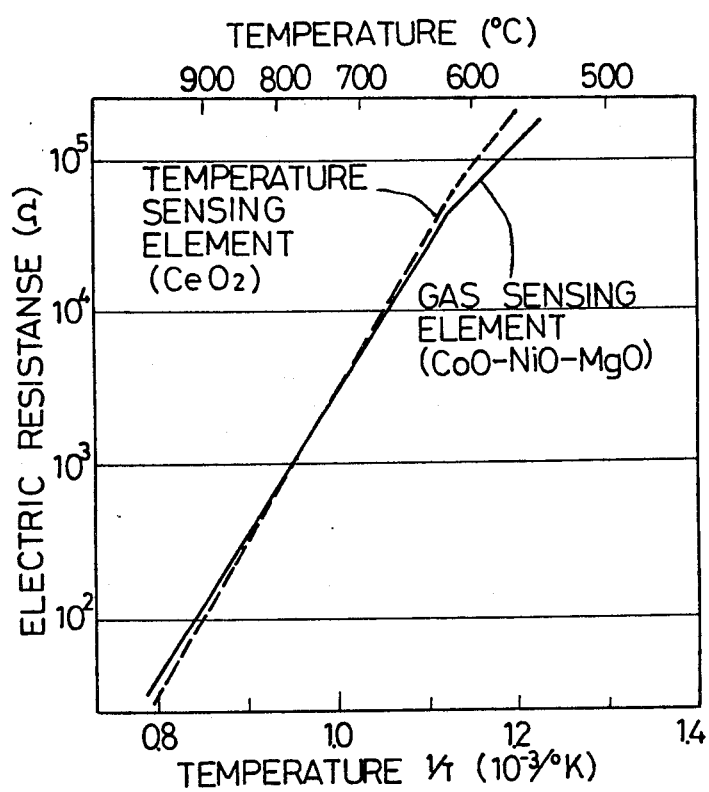
FIG. 15 is a graph showing temperature coefficient of resistance of the gas sensing element and the temperature sensing element of the sixth embodiment.

The result of measurement is shown in FIG. 15. As is apparent from FIG. 15, the resistance-temperature characteristic of the temperature sensing element 3 formed of cerium oxide is nearly equal to that of the gas sensing element 2 formed of cobalt monoxide, nickel monoxide and magnesium monoxide at 650° C. to 950° C.

FIG. 16 illustrates one example of the detecting circuit for producing electrical signals from the output voltage of the gas detecting sensor and supplying them into the fuel control device for the intake system of the internal combustion engine.

In FIG. 16, the reference numeral 19 designates an electric power source and the reference numeral 20 designates a control circuit which generates control signals after comparing the electrical signals supplied from the detecting sensor with a predetermined value.

The gas sensing element 2 and the temperature sensing element 3 is connected to each other in series.

At the terminal 6a (lead wire), the output voltage corresponding to the electric resistance of the gas sensing element 2 and the temperature sensing element 3 appears.

The heaters 5a, 5b are connected in parallel and grounded at the terminal 6e (lead wire).

Since the temperature sensing element 3 is embedded within the base body 1, the electric resistance thereof only depends on the temperature of the environment thereof without being affected by the partial pressure of oxygen gas.

And the electric resistance of the element 3 changes in substantially the same manner as that of the element 2 as the temperature is changed. Therefore, the gas detecting sensor of the fourth embodiment can precisely measure the air to fuel ratio without being affected by the temperature change.

Furthermore, since the resistance-temperature characteristic of the gas sensing element 2 agrees to that of the temperature sensing element 3 over a very wide temperature range from about 650° C to 950° C., the heaters 5a, 5b are controlled so as to operate at a temperature below 650° C. and above 950° C. by applying a predetermined voltage thereto.

FIGS. 17 and 18 illustrate a fifth embodiment of the sensor of the present invention.

In the fifth embodiment, the gas sensing element is formed of cobalt monoxide in which magnesium monoxide dissolves in solid phase, and the temperature sensing element is formed of zirconium oxide in which 10 mol % of niobium oxide dissolves.

As shown in FIGS. 17 and 18, on the base body 1, the electrodes 3a, 4a, 4b are formed. The temperature sensing element 3 is formed on the electrodes 3a, 4b while the gas sensing element 2 is formed on the electrodes 4a, 4b.

The surface of the temperature sensing element 3 is covered with a dense alumina film 101 so as not to be affected by the exhaust gases.

Within the base body 1, the heater 5b is formed.

Figure 19:
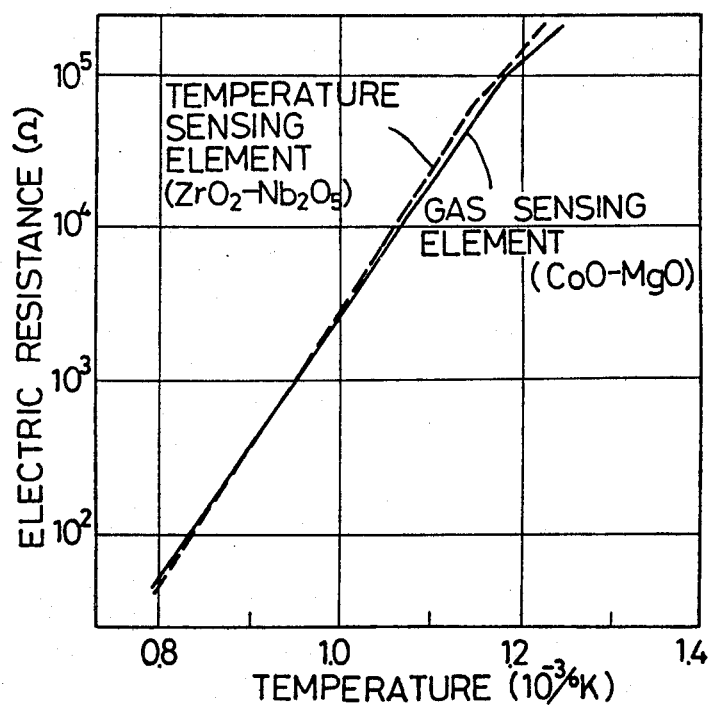
FIG. 19 is a graph showing temperature coefficient of resistance of the gas sensing element and the temperature sensing element of the seventh embodiment.

FIG. 19 illustrates the electric resistance of the gas sensing element 2 and that of the temperature sensing element 3 of the fifth embodiment with respect to the temperature change. As is apparent from FIG. 19, the resistance-temperature characteristic of the element 2 is substantially equal to that of the element 3. The base body can be formed of spinel, mullite, phorstellite, steatite or the like, other than alumina employed in the above described embodiments.

The gas sensing element can be formed of nickel monoxide, zirconium oxide, tin oxide, zinc oxide, cerium oxide lanthanchromite, niobium oxide or the like other than the material employed in the above described embodiments.

And the temperature sensing element can be formed of cobalt monoxide, nickel monoxide, zirconium oxide, tin oxide or the like other than the material employed in the above described embodiments.

The materials of the gas sensing element and the temperature sensing element are selected from the above various materials so that the resistance-temperature characteristic thereof is nearly equal to each other.

And the gas sensing element and the temperature sensing element can be formed of the same material.

The layer for covering the temperature sensing element is formed of the heat resistant and electrically insulating material, such as the material of glass matter, alumina, or spinel.

As described above, the gas detecting sensor according to the present invention is provided with a temperature sensing element having resistance-temperature characteristic nearly equal to that of the gas sensing element, which is formed so as not to be affected by the chemical constituent of exhaust gases.

The gas detecting sensor according to the present invention can measure the partial pressure of oxygen gas precisely without being affected by the temperature change of the environment thereof.

And in the gas detecting sensor according to the present invention, the gas sensing element and the temperature sensing element which are formed like a film, respectively, are retained by the base body, so that the structure of the sensor is simple and that the sensor can be easily produced.

Having now fully described the invention, it will be apparent to one of ordinary skill in the art that many changes and modifications can be made thereto without departing from the spirit or scope of the invention as set forth herein.

What is claimed is:

1. A gas detecting sensor for detecting the partial pressure of oxygen gas contained within exhaust gases discharged from an engine, comprising:
    a base member formed of ceramic material, which is mounted to an exhaust passage of said engine so as to be exposed to the exhaust gases, said base member being composed of a first and a second ceramic plates which are integrally combined by sintering;
    a film shaped first sensing element formed of ceramic material having an electrical characteristic in response to the partial pressure of oxygen gas, which is printed on the upper surface of said first ceramic plate;
    a film shaped second sensing element formed of ceramic material having a temperature coefficient of resistance similar to that of said first sensing element, which is printed on the upper surface of said second ceramic plate and which is to be combined with the under surface of said first plate; and
    an electric circuit wherein said first and second sensing elements are connected to an electric power source in series, output voltage being taken from an electric junction between said first and second sensing elements.

2. A gas detecting sensor according to claim 1, wherein:
    said first sensing element is formed of a material selected from the group consisting of cobalt monoxide, titanium oxide, nickel monoxide, zirconium oxide, tin oxide, zinc oxide, cerium oxide, lanthanchromite, niobium oxide, solid solution of cobalt monoxide and magnesium monoxide, and solid solution of cobalt monoxide, magnesium monoxide and nickel monoxide.

3. A gas detecting sensor according to claim 1, wherein:
    said second sensing element is formed of a material selected from the group consisting of cobalt monoxide, titanium oxide, nickel monoxide, zirconium oxide, tin oxide, cerium oxide, solid solution of zirconium oxide and niobium oxide, and solid solution of cobalt monoxide and magnesium monoxide.

4. A gas detecting sensor according to claim 1, wherein:
    said first and said second elements are formed of the same material as each other.

5. A gas detecting sensor according to claim 1, wherein:
    said base member is formed of alumina, spinel, mullite, phorstellite and steatite into a plate shape.

6. A gas detecting sensor according to claim 1, further comprising:
    a heating member for maintaining said first and second sensing elements within a predetermined temperature range which is embedded within said base member and/or formed on the upper surface of said base member, said heating member being connected to said first and second sensing elements in parallel.

7. A gas detecting sensor according to claim 6, wherein:
    said base member is composed of a first ceramic plate and a second ceramic plate, which are integrally combined by sintering;
    on the upper surface of said first plate, a first pair of film-shaped electrodes are printed and said first sensing element is printed so as to cover one end of each of said first pair of electrodes;
    on the upper surface of said second plate, which is to be combined with the under surface of said first plate, a second pair of film-shaped electrodes are printed, said second sensing element is printed so as to cover one end of each of said second pair of electrodes and said heating member is printed into a film shape so as to surround said second sensing element;
    the other end of one of said first pair of electrodes are electrically connected to the other end of one of said second pair of electrodes to form said electric junction; and
    a lead wire is connected to said electric junction for taking output voltage therefrom.

8. A gas detecting sensor according to claim 6, wherein:
    said base member is composed of a first ceramic plate and a second ceramic plate and a third ceramic plate which are integrally combined by sintering;
    on the upper surface of said first plate, a first pair of film-shaped electrodes are printed, said first sensing element is printed so as to cover one end of each of said first pair of electrodes; and a first film shaped heating member is printed so as to surround said first sensing element;
    on the upper surface of said second plate, which is to be combined with the under surface of said first plate, a second film-shaped heating member is printed so as to be connected to said first heating member in parallel;
    on the upper surface of said third plate, which is to be combined with the under surface of said second plate, a second pair of film-shaped electrodes are printed and said second sensing element is printed so as to cover one end of each of said second pair of electrodes;
    the other end of one of said first pair of electrodes are electrically connected to the other end of one of said second pair of electrodes to form said electric junction; and
    a lead wire is connected to said electric junction for taking output voltage therefrom.

* * * * *